United States Patent
Simon

(10) Patent No.: US 9,848,844 B2
(45) Date of Patent: Dec. 26, 2017

(54) ITERATIVE RECONSTRUCTION PROCESS

(71) Applicant: Carestream Health, Inc., Rochester, NY (US)

(72) Inventor: Richard A. Simon, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 123 days.

(21) Appl. No.: 14/879,136

(22) Filed: Oct. 9, 2015

(65) Prior Publication Data

US 2017/0100088 A1     Apr. 13, 2017

(51) Int. Cl.
*A61B 6/00* (2006.01)
*A61B 6/03* (2006.01)

(52) U.S. Cl.
CPC ............ *A61B 6/5258* (2013.01); *A61B 6/032* (2013.01); *A61B 6/4007* (2013.01); *A61B 6/4085* (2013.01)

(58) Field of Classification Search
CPC ..... A61B 6/5258; A61B 6/032; A61B 6/4007; A61B 6/4085
See application file for complete search history.

(56) References Cited

U.S. PATENT DOCUMENTS

| | | | | |
|---|---|---|---|---|
| 5,909,476 A | * | 6/1999 | Cheng | G06T 11/006 378/4 |
| 9,336,614 B1 | * | 5/2016 | Wollenweber | G06T 11/008 |
| 2003/0156684 A1 | * | 8/2003 | Fessler | A61B 6/032 378/210 |
| 2006/0122499 A1 | * | 6/2006 | Hristov | A61B 6/032 600/425 |
| 2007/0133747 A1 | * | 6/2007 | Manak | A61B 6/00 378/62 |
| 2008/0049891 A1 | * | 2/2008 | Yin | G06T 11/006 378/9 |
| 2008/0095301 A1 | * | 4/2008 | Kohler | A61B 6/027 378/4 |
| 2009/0225932 A1 | * | 9/2009 | Zhu | A61B 6/032 378/7 |
| 2010/0119139 A1 | * | 5/2010 | Bertram | G06T 11/005 382/131 |
| 2010/0331665 A1 | * | 12/2010 | Ladebeck | A61B 5/055 600/411 |

(Continued)

OTHER PUBLICATIONS

D. Kadrmast et al., "Truncation Artifact Reduction in Transmission CT for Improved SPECT Attenuation Compensation", Phys. Med. Biol., 40, 1995, pp. 1085-1104.

(Continued)

*Primary Examiner* — Sean Conner
*Assistant Examiner* — Pinalben Patel

(57) ABSTRACT

An iterative algorithmic method determines spatial distribution of attenuation values of an object based on measured projection data of the object. An algorithm generates estimated projection data based on an estimated spatial distribution of the attenuation values. Correction data is determined based on a difference between the measured projection data and the estimated projection data. Spatially extended correction data is back projected to update the estimated spatial distribution of the attenuation values. The algorithmic iterations continue until a stopping criterion is reached.

19 Claims, 6 Drawing Sheets

(56) References Cited

U.S. PATENT DOCUMENTS

| | | | |
|---|---|---|---|
| 2011/0103542 A1* | 5/2011 | Allmendinger | A61B 6/032 378/4 |
| 2011/0255765 A1* | 10/2011 | Carlson | A61B 5/0064 382/131 |
| 2013/0094735 A1 | 4/2013 | Zamyatin et al. | |
| 2013/0329856 A1* | 12/2013 | Kuwahara | A61N 5/1039 378/62 |
| 2014/0334705 A1* | 11/2014 | Ishii | A61B 6/032 382/131 |
| 2015/0025370 A1* | 1/2015 | Neukirchen | A61B 6/032 600/425 |
| 2015/0190108 A1* | 7/2015 | Li | A61B 6/022 378/41 |
| 2015/0228092 A1* | 8/2015 | Claus | G06T 11/006 382/131 |
| 2016/0262713 A1* | 9/2016 | Flohr | A61B 6/5205 |
| 2016/0302751 A1* | 10/2016 | Grant | A61B 6/5205 |

OTHER PUBLICATIONS

Y. Zhang et al., "Artifact Reduction Methods for Truncated Projections in Iterative Breast Tomosynthesis Reconstruction", NIH-PA Author Manuscript, 2009, pp. 1-21.

Y. Lu et al., "A Diffusion-based Truncated Projection Artifact Reduction Method for Iterative Digital Breast Tomosynthesis Reconstruction", Phys. Med. Biol., 58, 2013, pp. 569-587.

* cited by examiner

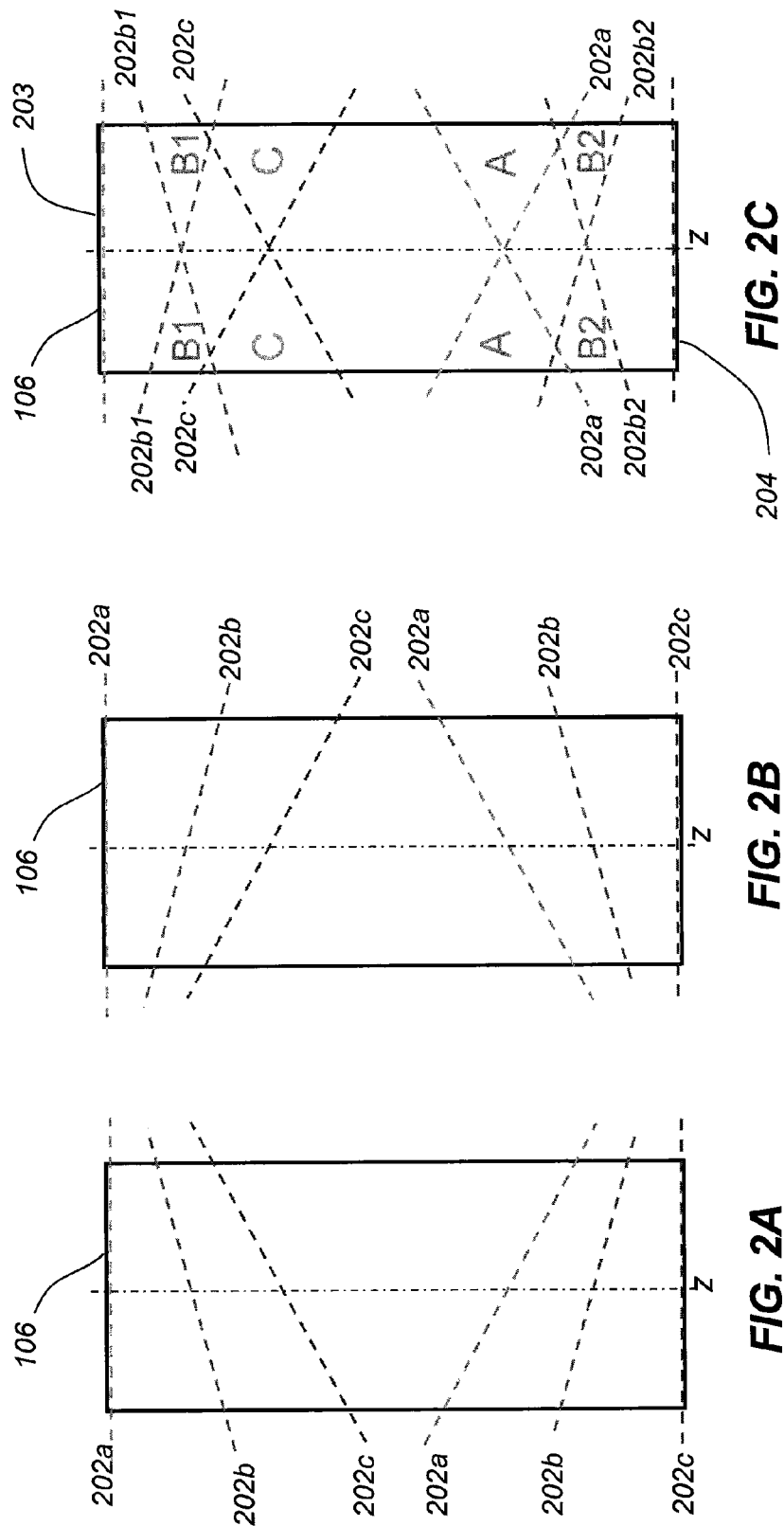

ITERATIVE RECONSTRUCTION PROCESS

BACKGROUND OF THE INVENTION

The subject matter disclosed herein relates to three dimensional radiographic imaging and, in particular, to generating accurate volume images using iterative reconstruction algorithms during tomosynthesis and tomography image processing, such as in cone beam computed tomography (CBCT) systems using one or more radiation sources.

In radiographic image reconstruction, interior reconstruction, also known as limited field of view reconstruction, is a technique to correct truncation artifacts caused by limiting image data to a partial field of view. The reconstruction focuses on an area of the image referred to as the region of interest, which may typically be proximate to a boundary of the field of view. Interior reconstruction can be applied to various radiographic image types using one or more of various methods.

Cone beam reconstruction algorithms have been implemented in techniques such as filtered back projection algorithms. Approximate cone-beam reconstruction algorithms are important in the cases of incomplete scanning geometry and partial field of view coverage. Approximate reconstruction is usually associated with higher computational efficiency and less image artifacts such as noise and ringing. Adaptations have been made for cone beam reconstruction using circular scanning. Some existing cone-beam algorithms require that projections be complete at least along one direction and are therefore inapplicable in partial field of view cases where objects are larger than the cone beam field of view (cone beam angle) as defined by effective detection area and x-ray source position.

Continuous cone-beam projection measurements can be approximated as a set of digital image values captured at a 2D digital detector comprising a grid of photosensitive detector elements, each of which comprises a sum of weighted values of voxels exposed by, or proximate to, a corresponding path of an x-ray beam. A cone-beam imaging geometry is specified, including the distance between the source and the digital detector, the dimensions of the detector, as well as the distribution of the photosensitive elements over the receiving surface of the digital detector. An x-ray beam path may be computationally divided at equidistance points along its length equivalent to a voxel side length. The value of each dividing point may be an interpolation of the values of its nearest voxel neighbors. A 2D image projection datum associated with an x-ray beam path may be modeled as the sum of incremental attenuation contributions from all the dividing points (voxels) along the path.

Discrepancies between measured and estimated projection data may be computed, for example, as ratios or normalized differences for each combination of detector and source locations. These discrepancies (either ratios or differences) may be back projected over a stored 3D digital image. Known object image data may be combined to generate an updated image, and reconstruction errors may be estimated in image and/or projection domains. Decisions may be made to continue iterations or to output a reconstructed image for viewing at a workstation, for example, or any other suitable device or system, or for further processing.

In either reprojection or back projection, representative x-rays may be evenly divided with a pre-specified interval length (for example, the voxel side length as described herein) being consistent with the discrete cone-beam imaging model. In reprojection, the voxel values of eight nearest neighbors of each dividing point may contribute to the projection value using an interpolation technique. In back projection, a projection value may be additively redistributed to the eight nearest neighbors of each dividing point after weighting with corresponding interpolation coefficients.

In a scanning sequence for each x-ray projection image obtained, a field of view boundary is determined by the position and edges of the digital detector and the x-ray source location. During updating of voxels using a given projection, only voxels within the field of view will be updated, whereas the voxels outside the field of view maintain their previous values. Voxels may be updated at a greater frequency than adjacent or closely neighboring voxels. As a result, the number of times a given voxel is updated during the reconstruction process is dependent upon the location of the voxel in the reconstruction volume. The spatial variation of update counts per voxel generates artifacts in the final reconstructed volume image which typically occurs along spatial boundaries where the update counts between voxels shows a high discrepancy.

The discussion above is merely provided for general background information and is not intended to be used as an aid in determining the scope of the claimed subject matter.

BRIEF DESCRIPTION OF THE INVENTION

The present invention solves the problem of truncated projections artifacts that occur with iterative reconstructions. The truncated projection artifacts arise from the transition between the exposed and unexposed parts of the imaged volume which varies as the x-ray source position changes such as in a circular x-ray scanning sequence. Embodiments of the invention are applicable to tomosynthesis and CBCT products that use an iterative reconstruction algorithm. Embodiments of the invention lead to a simple, efficient, and CPU friendly way of correcting truncated projection artifacts. In general, for iterative reconstructions, a current estimated 3D image volume is used to generate estimated 2D projection images which, along with actual measured projection images, are compared to generate error images, or correction images, that, in turn, are used to update the voxels of the current estimated 3D image volume. Extrapolating the error image virtually increases the field of view and enables more voxels to be updated, thereby decreasing update count variances between neighboring voxels. This helps to mitigate the truncated projections artifacts that appear in the iterative reconstruction of a CBCT imaging system.

By extrapolating the error images at the top, side and/or bottom borders, for example, via a novel extrapolation algorithm, the calculated error image is extended to virtually increase the field of view. The top, side and/or bottom rows of the calculated error image (or correction image) are progressively blurred into the extended region. This extrapolated image is then used to update the current estimated 3D volume reconstruction. The algorithm repeats until one or more stop criteria are satisfied.

Thus, the measured projection images enable more voxels to be updated using each projection image. The error image is used to update the voxels in the projection's field of view and then on a slice-wise basis the updated voxels are used to correct the voxels which were outside the projection's field of view. In one embodiment of the present invention, a method of determining a spatial distribution of attenuation values of an object using a plurality of projection images of the object is disclosed. An advantage that may be realized in the practice of some disclosed embodiments is an improved iterative reconstruction algorithm that reduces axial artifacts in an image that has been reconstructed from cone beam data.

In one embodiment, a method of determining a three dimensional spatial distribution of attenuation values of an object comprises obtaining an estimate of the spatial distribution of attenuation values and capturing a plurality of projection images of the object. One or more estimated projection images are generated and are each associated with one of the plurality of captured projection images. The estimated projection images are generated using the estimate of the spatial distribution of attenuation values. A correction image is generated based on the one or more estimated projection images and its associated captured projection image. An extended correction image is generated by extrapolating image data in the correction image. The estimate of the spatial distribution of attenuation values is then updated using the at least one extended correction image.

In another embodiment, a method of determining a spatial distribution of attenuation values of an object comprises obtaining an initial estimate of the spatial distribution of attenuation values of the object and capturing a plurality of projection images of the object using an imaging system having an associated field of view and an associated field of view size. The following steps are then repeated until a stop criterion is satisfied: generating one or more estimated projection images using a current estimate of the spatial distribution of attenuation values, comparing the one or more estimated projection images with the captured projection images to generate correction image data corresponding to the field of view size, extrapolating the one or more correction images to extend the correction image data beyond its corresponding field of view size, and generating a current estimate of the spatial distribution of attenuation values using the extended correction image data.

In another embodiment, a method of determining a three dimensional spatial distribution of attenuation values of an object is disclosed, using a radiographic imaging system. The method includes obtaining an estimate of the spatial distribution of attenuation values and capturing a plurality of projection images of the object using each of two or more x-ray sources. A plurality of estimated projection images is generated whereby each corresponds to a position of one of the x-ray sources and each is associated with one of the plurality of captured projection images. The estimated projection images are generated using the estimate of the spatial distribution of attenuation values. A plurality of correction images are generated based on the plurality of estimated projection images and their corresponding captured projection image and then an extended correction image is generated by extrapolating data in the correction image. The estimate of the spatial distribution of attenuation values is updated using the extended correction image.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. The drawings below are intended to be drawn neither to any precise scale with respect to relative size, angular relationship, relative position, or timing relationship, nor to any combinational relationship with respect to interchangeability, substitution, or representation of a required implementation. It is to be noted that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 2A-C are schematic diagrams of exemplary x-ray paths through an object to be volume reconstructed in the exemplary CBCT imaging system of FIGS. 1A-B;

DETAILED DESCRIPTION OF THE INVENTION

Figure 1A:
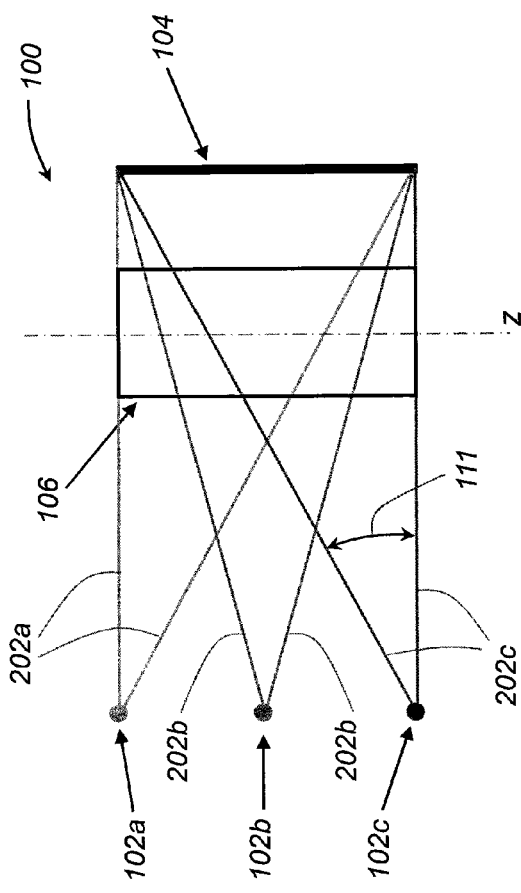
FIGS. 1A-1B are schematic diagrams of an exemplary multi-source imaging system.

With reference to FIG. 1A there is illustrated a schematic diagram of a tomographic imaging system 100 comprising one or more radiographic energy (x-ray) sources 102a-c aimed at an object 106 to be radiographically imaged. A digital radiographic (DR) detector 104 is positioned in a known and predetermined geometric relationship with the x-ray sources 102a-c wherein the object 106 to be imaged is positioned therebetween. In one embodiment, the x-ray sources 102a-c and the DR detector 104 may form a portion of a cone beam computed tomography (CBCT) imaging system 100, whereby one or more of the x-ray sources 102a-c and the detector 104 are configured to revolve about an imaging axis z while capturing a plurality of digital projection (2D) images of the object 106 in the detector 104, as is well known in the digital radiography arts. The captured images may be processed in, or transmitted by, the detector 104. If transmitted, the detector may use wired or wireless transmission to an attached computer system for processing, such as for reconstructing a 3D image from the captured projection images.

Figure 1B:
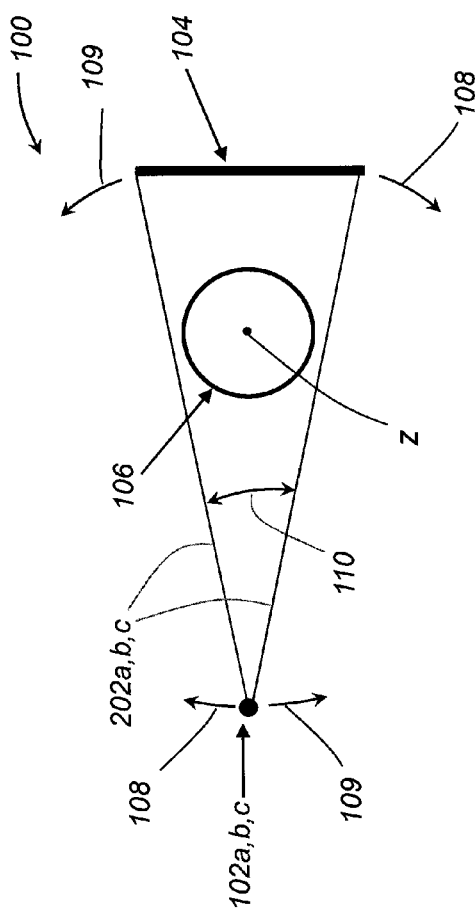

In one embodiment, the object to be imaged 106 is positioned so as to coincide with the imaging axis z, although such positioning is not required, and adequate images of the object 106 may be captured and/or reconstructed by the system 100 if the object 106 is positioned proximate to the imaging axis z. The one or more x-ray sources 102a-c may each be configured to controllably emit, or fire, an x-ray beam 202a-c, respectively, such as a cone beam, aimed at object 106 and toward the DR detector 104. The shapes of the x-ray beams 202a-c are not intended to illustrate a limiting shape of the x-ray beams 202a-c. Rather, they are intended to highlight the portion of the emitted x-ray beams that penetrate the object 106. FIG. 1B is a schematic top view of the imaging system 100 illustrating an embodiment of the imaging system 100 whereby the x-ray sources 102a-c are arranged collinearly in a line parallel to the imaging axis z.

In one embodiment, to complete a CBCT scan of the object 106, at least one of the sources 102a-c are selectively and controllably fired multiple times while simultaneously revolving both the selected one or more of sources 102a-c and the detector 104 about axis z for at least a portion of one revolution thereabout, i.e., 360° or less, in either of the directions indicated by arrows 108 or 109, while maintaining the selected one or more sources 102a-c and detector 104 diametrically opposed in relation to the axis z. Each firing of the selected one or more of the sources 102a-c generates a different radiographic projection image (2D) of the object 106, depending on its angular position, that is digitally captured by detector 104. In one embodiment, the selected one or more of the sources 102-a-c is fired multiple times at angular points equidistant from each other as it revolves about axis z for one complete revolution. In one embodiment, the selected one or more of the sources 102a-c is fired 360 times during one revolution (360° scan) about axis z, each firing occurring substantially one degree apart. In another embodiment, the selected one or more of the sources 102a-c is each fired 200 times during one revolution about axis z, each firing also occurring at angular points substantially equidistant from each other. In another embodiment, the selected one or more of the sources 102a-c is each fired 3600 times during one revolution about axis z, each firing also occurring at angular points substantially equidistant from each other. It will be recognized by persons skilled in the art that any number of images may be captured during one revolution of a selected one or more of the sources 102a-c and detector 104, limited only by the mechanical and electrical characteristics of the tomographic imaging system 100. It will be appreciated by one skilled in the art that x-rays are emitted from the one or more sources 102a-c with a representative predetermined cone beam angle 110 and a representative predetermined fan beam angle 111. During the digital image data acquisition procedure, which may be referred to herein as an imaging scan, a 360 scan, or a scanning sequence, for example, the one or more sources 102a-c travel over a predetermined circular trajectory in relation to the object 106 in unison with the detector 104 such that the detector 104 acquires and transmits circular cone beam image data.

It is well known that imaging systems as depicted in FIGS. 1A-B are operable using only one of the x-ray sources 102a-c. Thus, the embodiments disclosed herein are not limited only to using multiple x-ray source 102a-c imaging systems 100 and are equally applicable to imaging systems using only one, or only two, of the x-ray sources 102a-c. Those having ordinary skill in the art will recognize that the system depicted in FIG. 1 may be modified, as exemplified herein (FIG. 5), without departing from the scope of the invention claimed herein.

FIGS. 2A-C are schematic diagrams illustrating portions of the object 106 that are captured in radiographic projection images using the imaging system 100, i.e., portions of object 106 that are within a field of view for each of sources 102a-c. FIG. 2A illustrates: a side view of the portion of the object 106 that is irradiated by the source 102a, i.e., is in the field of view of source 102a relative to detector 104 (not shown), at a point in time during a revolution of the imaging system 100 when the source 102a is positioned on one side of the object 106, as indicated by the dashed lines 202a which represent an x-ray beam emitted by the source 102a; a side view of the portion of the object 106 that is irradiated by the source 102b, at a point in time during a revolution of the imaging system 100 when the source 102b is positioned on one side of the object 106, as indicated by the dashed lines 202b which represent an x-ray beam emitted by the source 102b; and a side view of the portion of the object 106 that is irradiated by the source 102c, at a point in time during a revolution of the imaging system 100 when the source 102c is positioned on one side of the object 106, as indicated by the dashed lines 202c which represent an x-ray beam emitted by the source 102c. FIG. 2B illustrates: a side view of the portion of the object 106 that is irradiated by the source 102a, at a point in time during a revolution of the imaging system 100 when the source 102a is positioned on a side of the object 106 opposite that illustrated in FIG. 2A, as indicated by the dashed lines 202a which represent the x-ray beam emitted by the source 102a; a side view of the portion of the object 106 that is irradiated by the source 102b, at a point in time during a revolution of the imaging system 100 when the source 102b is positioned on a side of the object 106 opposite that illustrated in FIG. 2A, as indicated by the dashed lines 202b which represent the x-ray beam emitted by the source 102b; and a side view of portion of the object 106 that is irradiated by the source 102c, at a point in time during a revolution of the imaging system 100 when the source 102c is positioned on a side of the object 106 opposite that illustrated in FIG. 2A, as indicated by the dashed lines 202c which represent the x-ray beam emitted by the source 102c.

FIG. 2C illustrates a side view of a volumetric portion A of the object 106 that is not irradiated (exposed) by the source 102a from all points of its revolution about axis z but is irradiated by a subset of exposures performed by the source 102a, i.e., the volumetric portion A is not in the field of view of source 102a relative to detector 104 (not shown) at all positions of the source 102a and detector 104 during a complete 360° scan, i.e., one revolution, of the object 106, as described herein with reference to FIG. 1B. The volumetric portion A is represented by the region between intersecting dashed lines 202a. The region of object 106 above the dashed lines 202a (above volumetric portion A) up to the top surface 203 of object 106 is irradiated by all firings of source 102a during its revolution. FIG. 2C further illustrates a side view of a volumetric portions B1, B2, of the object 106 that are not irradiated by the source 102b from all points of its revolution about axis z but is irradiated by a subset of exposures performed by the source 102b, i.e., the volumetric portions B1, B2, are not in the field of view of source 102b relative to detector 104 (not shown) at all positions of the source 102b and detector 104 during a complete 360° scan, i.e., one revolution, of the object 106, as described herein with reference to FIG. 1B. The volumetric portions B1, B2, are represented by the regions between intersecting dashed line pairs 202b1 and 202b2, respectively. The region of object 106 between the dashed lines 202b1 and 202b2 (between volumetric portions B1 and B2) is irradiated by all firings of source 102b during its revolution. FIG. 2C further illustrates a side view of a volumetric portion C of the object 106 that is not irradiated by the source 102c from all points of its revolution about axis z but is irradiated by a subset of exposures performed by the source 102c, i.e., the volumetric portion C is not in the field of view of source 102c relative to detector 104 (not shown) at all positions of the source 102c and detector 104 during a complete 360° scan, i.e., one revolution, of the object 106, as described herein with reference to FIG. 1B. The volumetric portion C is represented by the region between intersecting dashed lines 202c. The region of object 106 below the dashed lines 202c (below volumetric portion C) down to the bottom surface 204 of object 106 is irradiated by all firings of source 102c during its revolution.

Figure 6B:
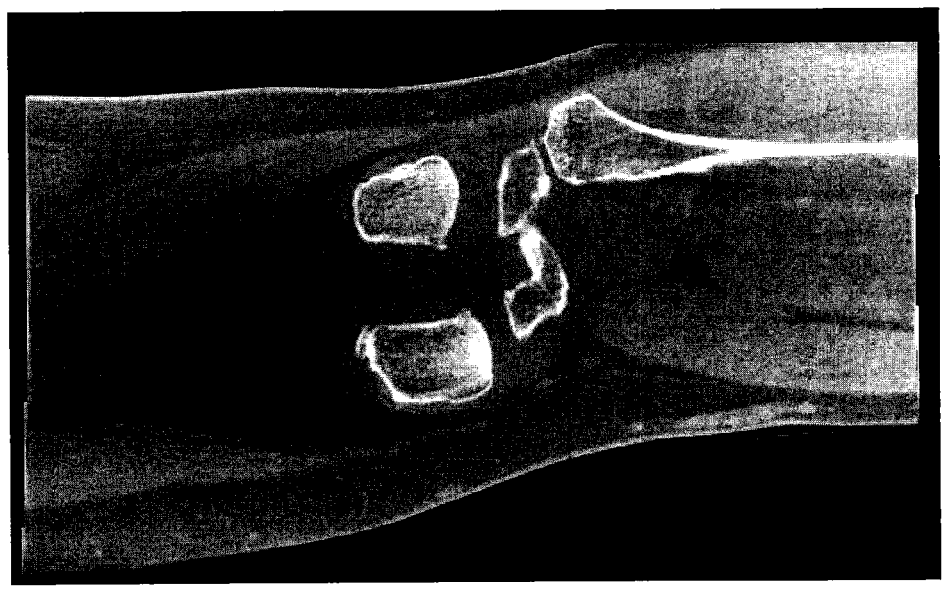
FIGS. 6A-6B are radiographic images illustrating exemplary artifacts caused by a prior art iterative reconstruction algorithm and an image corrected by using an exemplary iterative reconstruction algorithm of the present invention, respectively.
Figure 6A:
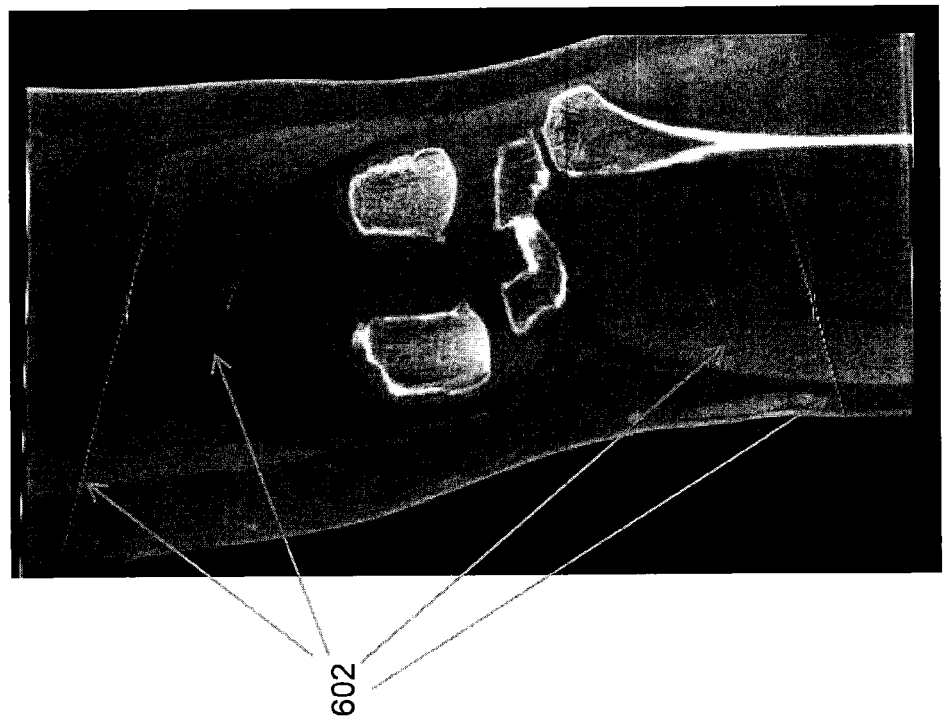

The boundaries of volumetric regions A, B, C, may cause artifacts to appear in radiographic images due to a variance in the number of times neighboring voxels are updated during the iterative reconstruction process, which is dependent upon the location of the voxel in the reconstruction volume. The spatial variation of update counts per voxel occurs along the spatial boundaries of volumetric regions A, B, C. The truncated projection artifacts described herein arise from the transition between these exposed and unexposed parts of the imaged volume which varies as the x-ray source position changes during one revolution about the axis z, as illustrated by the artifacts 602 in FIG. 6A. An iterative reconstruction algorithm disclosed herein is useful to correct the artifacts 602 as shown in the radiographic image of FIG. 6B where they no longer appear.

Figure 3:
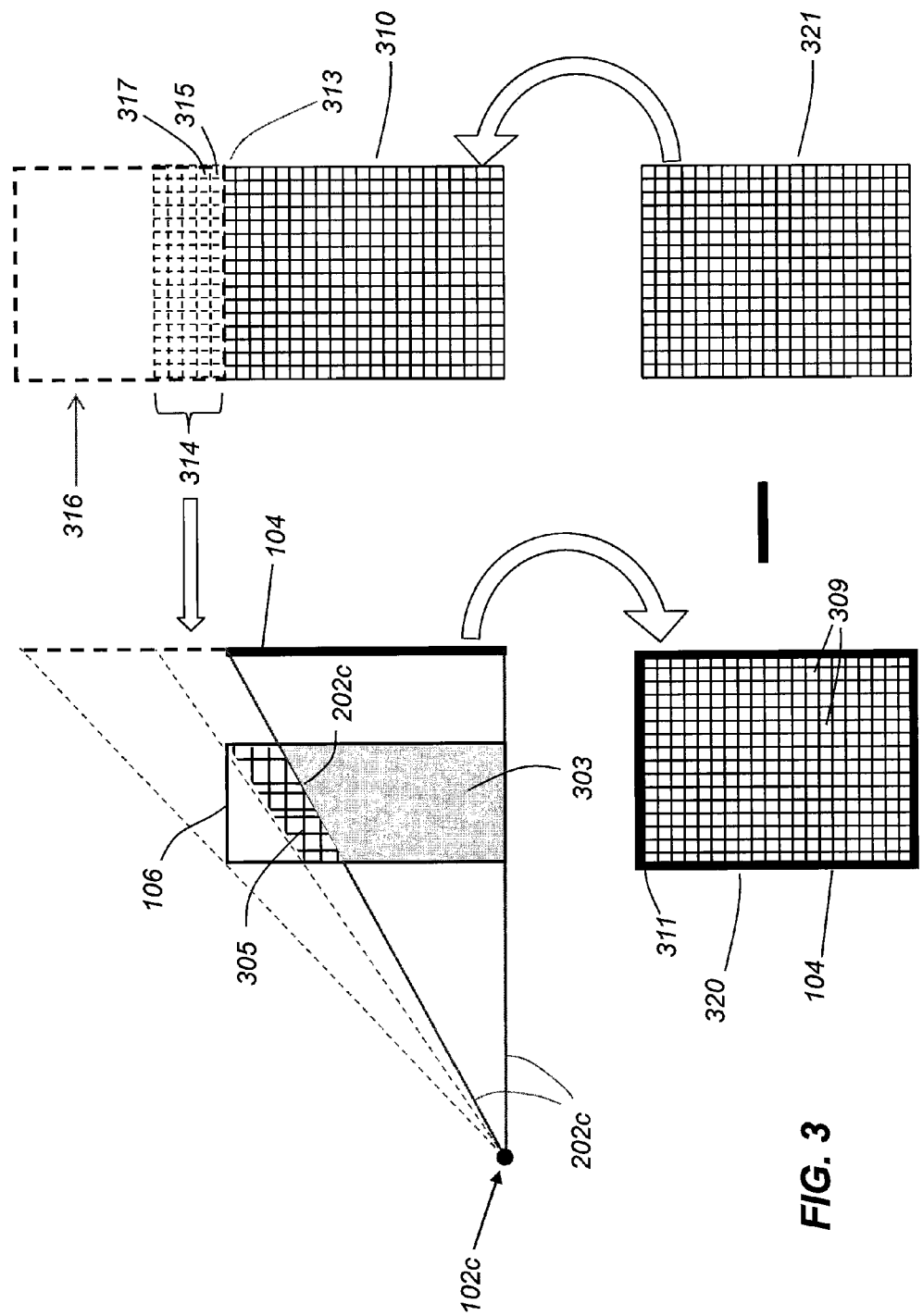
FIG. 3 is a step wise schematic diagram of generating extrapolated extended correction data for reconstruction.

FIG. 3 is a schematic diagram illustrating an exemplary projection image capture of object 106 using the source 102c and detector 104 (side view) of imaging system 100. The following description is similarly applicable to a projection image capture using any one or more of sources 102a-c of imaging system 100 as disclosed herein. The shaded portion 303 of object 106 within the field of view of source 102c and digital detector 104 is that portion exposed to an x-ray beam 202c and effectively captured by digital detector 104, resulting in actual projection image data 320 stored in the detector 104 (front view). The digital detector 104 comprises a two dimensional array of pixels 309, which may be said to be arranged in a flat panel grid of rows and columns, for capturing a radiographic projection image of the portion 303 of object 106, as is well known by those skilled in the art. Estimated 2D image data 321 of object 106 is generated using the current estimated spatial distribution of attenuation values by logically simulating the known geometrical arrangement of the imaging system 100 components that were used to capture the actual projection image data 320. The estimated 2D image data 321 of object 106 and the projection image data 320 of object 106 are compared to generated a difference image or, as referred to herein, a correction image 310 comprising correction data representing a magnitude of the difference between the estimated 2D image data 321 of object 106 and its projection image data 320.

Using algorithms disclosed herein, pixels at the top row 313 of correction image 310, corresponding to projection image pixels proximate an upper edge 311 of digital detector 104, may be processed using algorithms disclosed herein to extrapolate extended correction pixel data 314, thereby virtually extending a field of view provided by source 102c and detector 104. By using the extended pixel correction data 314 in a back projection reconstruction step, it will effectively reduce variance in voxel updates along the x-ray beam 202c boundary at the top of shaded portion 303, which variance, uncorrected, produces the truncated projection artifacts 602 as described herein. As described herein, the extended correction data 314 may be used in iterative reconstruction to update a 3D reconstruction of object 106 into portion 305 of the object 106 above the x-ray beam 202c boundary. Extended correction data 314 may be generated up through 2D area 316, or further, to provide 2D data for use in reconstructing 3D regions of the object 106 even further above the extended reconstructed portion 305. In one embodiment, the estimated 2D image data 321 of object 106 includes the same resolution of image data as the projection image data 320 so that there exists a one-to-one correspondence for each pixel 309 datum. In one embodiment, the correction image 310 data includes the same resolution as the projection image data 320 to maintain the same one-to-one correspondence for each pixel 309 datum.

Figure 4:
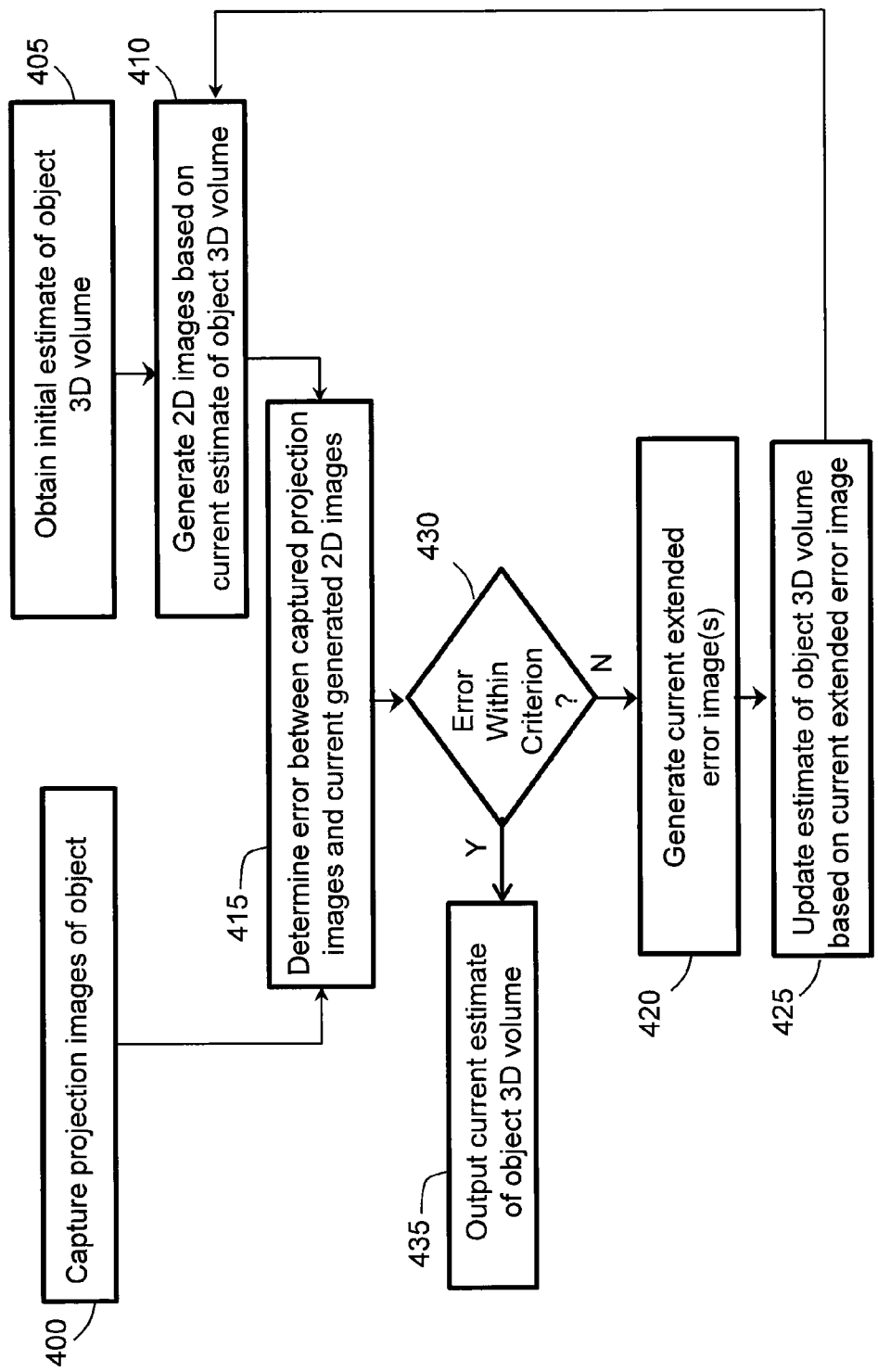
FIG. 4 is a flow chart of an exemplary algorithm for volume reconstruction.

FIG. 4 illustrates an exemplary embodiment of an algorithm for reducing truncated projection image artifacts as described herein. It will be understood that the steps described in FIG. 4 are not all required to be performed in one continuous process or workflow, and that actual or virtual image capture and image generation or reconstruction may be performed at different times and stored for later access and continuation of the process steps of the algorithm. Alternatively, they may be performed in a single continuous process. In one embodiment, a plurality of two dimensional (2D) radiographic projection images of the object 106 are captured, at step 400, by the detector 104 using an imaging system similar to the imaging system 100 described herein using one or more of the radiographic energy sources 102a-c. The captured images may be electronically stored in the detector or in an associated computer system. At step 405, an initial estimated 3D volume image, which may be referred to as a seed image, of the object 106 is obtained. As described herein, the initial estimated 3D volume image is repeatedly updated until a satisfactory 3D reconstruction image is completed. The estimated 3D volume image of the object 106 may be represented as a plurality of spatially distributed voxels each of which represent a 3D datum which, when combined and presented altogether on a digital monitor or display, depict a 3D representation of the object 106, which may also be referred to herein as a reconstruction image. Each of the voxels may be said to store a datum that corresponds to an attenuation value. The attenuation value represents a magnitude of x-ray absorption, or attenuation, of that interior volume portion of the object 106 represented by the voxel. Complete voxel data may be stored electronically in the detector or in an associated computer system. Thus, step 405 may include obtaining an estimated spatial distribution of attenuation values to be used as a starting set of 3D data representing object 106.

The estimated spatial distribution of attenuation values may be obtained in a variety of ways. The estimated spatial distribution of attenuation values may be set to a common value, such as zero or one (e.g. all the voxels are set to 0 or 1), or some other value. The estimate of the spatial distribution of attenuation values may set to a predetermined distribution of values selected to approximate a distribution that may best represent the object in a general sense, for example, taking into consideration an expected geometry or shape of the object to be imaged. The estimate of the spatial distribution of attenuation values may be retrieved from a database having stored therein any number of representative distributions of attenuation values. The estimate of the spatial distribution of attenuation values may be obtained by using a filtered back projection algorithm applied to one or more captured projection images of the object 106 obtained via step 400. Such captured projection images of the object 106 may have been digitally captured and stored previously, or may be captured at the time of a patient examination requiring a 3D reconstruction. By whatever means the initial 3D distribution of attenuation values or object 106 volume estimate is obtained, at step 410 it may be used to generate one or more 2D estimated images corresponding to the captured projection images obtained in step 400, as explained herein, representing one or several viewing angles of the initial estimate of the spatial distribution of attenuation values.

In one embodiment, a method of determining a spatial distribution of attenuation values of an object 106 using a plurality of actual stored projection images of the object is disclosed. One or more sets of projection images of the object may be digitally captured and electronically stored for use with the present algorithm or, if previously captured and stored, the projection images of the object may be retrieved from electronic storage as described herein in relation with step 400. Each of the captured projection images of the object may be digitally captured and indexed with a value representing a corresponding revolution capture angle. If a multi-source imaging system 100 is used, i.e., having multiple x-ray sources 102*a-c*, then an x-ray source identifier may also be associated (indexed) with each captured projection image together with the value representing a corresponding revolution capture angle.

For each of the captured projection images of the object 106, taking into account the geometry of the system 100 during image capture, a corresponding estimated 2D image may be generated, at step 410, based on the estimated 3D volume image of the object, i.e., its estimated spatial distribution of attenuation values. A computer system having stored therein the estimated spatial distribution of attenuation values may include parameters representing a geometry of the imaging system 100 to calculate pixel values for the estimated 2D image. In one embodiment, the parameters may include a height of an x-ray source 102*a-c* relative to the detector 104, a distance between the x-ray source 102*a-c* and the detector 104, a distance between the x-ray source 102*a-c* and the object to be imaged 106, a distance between the x-ray source 102*a-c* and the imaging axis z, an angular relation between the source 102*a-c* and the detector 104, such as a revolution angle, as well as other parameters.

At step 415, using the electronically stored estimated 2D images and their corresponding actual captured projection images, one or more 2D correction images may be generated which each represent an error magnitude as between pixels of the estimated 2D images and their corresponding actual projection images. The error magnitude may be determined several ways, for example, as a subtractive difference image wherein a difference between pixel values of the estimated 2D image and its corresponding actual projection image is determined; a mathematical ratio image wherein a proportion between the estimated 2D image and its corresponding actual projection image is determined; or a percentage image wherein a percentage difference of some aspect as between the estimated 2D image and its corresponding actual projection image is determined. Similarly, an average of any such determined values may be calculated to form one or more correction images. In any case, the correction image or images each comprise a set of data that represents an error magnitude between pixels of an estimated 2D image and its corresponding actual projection image.

The correction image may be extrapolated in at least one dimension at step 420, e.g. it is extended from its top, bottom, or side edge, such as illustrated in FIG. 3, so that the pixel values at one or more selected top, bottom, or side borders are extended. Methods for extrapolating or extending a digital image are known and, in one embodiment, an extrapolation algorithm may include adding a row of pixel values to an edge row or column of pixels of a correction image by simply repeating the pixel values that are in the preceding row or column of pixels, respectively. In one embodiment, a formula may be used to linearly or non-linearly modify pixel values for each added, or extended, row or column of pixels with respect to the immediately preceding row or column, such as using a roll off function. In another embodiment, pixels values in a correction image may be linearly or nonlinearly extrapolated into the rows and/or columns surrounding the correction image.

In one embodiment, the correction image 310 is extended using the following extrapolation procedure based upon diffusing the correction image 310 into regions bounding the borders of the correction image; for example diffusing the correction image data of row 313 into region 316. The pixels values at the top, bottom, one or both of the sides, or a combination thereof, are extended by sequentially replicating and blurring the pixel values of a preceding row or column and assigning them to the next row or column, respectively. For example, in FIG. 3, the correction image pixel values of the row 313 are replicated and blurred and assigned to the next row 315. The pixel values of row 315 are then replicated and blurred and assigned to row 317. This procedure is continued until the correction image has been extended by a preselected specified number of rows. As described herein, the extended correction image data 314 is stored in electronic digital memory locations logically associated with rows of pixel data for the correction image 310.

At step 425, the estimate of the spatial distribution of attenuation values (estimated 3D object volume) may be updated using the currently extended correction image to generate a current estimate of the spatial distribution of attenuation values. With reference to FIG. 3, this results in updating voxel values corresponding to the region 305 provided by virtually extending the field of view of the object 106 using extrapolated data 314. In one embodiment, the current estimate of the spatial distribution of attenuation values is updated by back projecting the extended correction image into the latest estimate of the spatial distribution of attenuation values to generate the current estimate of the spatial distribution of attenuation values. Thus, the previous estimate of the spatial distribution of attenuation values may be replaced with the current estimate of the spatial distribution of attenuation values to generate estimated 2D images in step 410. As described herein, the algorithm loops back to step 410 and repeats the step of generating estimated 2D images using the current estimate of the spatial distribution of attenuation values. A new current correction image is then determined by repeating step 415, and so on, until the algorithm satisfies a predetermined stop criterion.

A predetermined stop criterion may be used to monitor progression of the algorithm described herein at any step of the algorithm. In one embodiment, satisfaction of the stop criterion may be determined at step 430, after step 415. The stop criterion may be determined to be satisfied when a selected one or more of the pixel values of the current correction image (whose data may represent an error magnitude per pixel) reaches or surpasses a threshold, such as a minimum value; when successive estimates of the spatial distribution of attenuation values are determined to converge; when a difference between a current (last updated) and a previous estimate of the spatial distribution of attenuation values reaches a threshold; or when a preselected number of iterations of the algorithm are performed, for example, or a combination thereof.

The stop criteria may also be based on one or more correction images. After generating the latest correction image, or error image, it may be determined, at step 430, that a difference between the generated projection images and the actual projection image falls below an acceptable threshold, which itself may be electronically stored as numerical data. In one embodiment, the threshold criterion or criteria may be based upon the correction image, and so the determination at step 430 may be performed by evaluating the correction image. For example, a correction magnitude represented in the stored correction image data may approach, or reach, a zero value. If the correction image data or any one or more of the stop criteria are satisfied then the current estimate of the spatial distribution of attenuation values (current estimate of the object 3D volume) may be used as the final reconstructed 3D volume image of the object 106 and output, at step 435.

In one embodiment, algebraic methods may be used to formulate the reconstruction problem such as finding the estimated spatial distribution of attenuation values f, which may be referred to herein as the reconstruction image or the 3D volume image, using the actual projection images data p. These methods are designed to solve the following simultaneous system of equation:

$$p = Af \quad (1)$$

where A is the forward projection matrix.

The reconstruction image f is reconstructed by computing an estimate that minimizes the following objective function:

$$f^* = \operatorname*{argmin}_{f>0}\left\{\frac{1}{2}\|Af - p\|^2\right\} \quad (2)$$

The optimization can be solved using a gradient descent method given by the following iterative solution:

$$f^{k+1} = f^k - \delta A^T(Af^k - p) \quad (3)$$

where $\delta$ is a constant update coefficient. This exemplary method can be used to extend the correction images generated by $Af^k - p$ before back projecting the correction images into the reconstruction image.

Model Bases Iterative Reconstruction (MBIR) algorithms typically work by first forming an objective function that incorporates an accurate system model, statistical noise model, and a prior image model. The reconstruction image f is reconstructed by computing an estimate that minimizes the following objective function:

$$f^* = \operatorname*{argmin}_{f>0}\left\{\mu R(f) + \frac{1}{2}\|Af - p\|_W^2\right\} \quad (4)$$

The first term on the right hand side is a regularize/prior R(f) that encourages the smoothness/prior information in the image reconstruction. The second term is a data fidelity term that encourages similarity to the original noisy projection data p. The data fidelity term incorporates the accurate system model in the forward projection matrix A and the statistical noise model is incorporated into the statistical weighting matrix W. The scalar $\mu$ controls the balance between the data and prior term and thus the resulting noise/smoothness in the reconstructed image.

Many types of algorithms can be used for minimizing the objective function defined by (4). The forward-backwards operator splitting technique is one way of minimizing the objective function. The operator splitting technique simplifies and improves the computational efficiency of the minimization by splitting the regularizer term and data term into the following two step algorithm:

$$v^{k+1} = f^k - \delta A^T W(Af^k - p) \quad (5)$$

$$f^{k+1} \leftarrow \operatorname*{minarg}_{f>0}\left\{\mu R(f) + \frac{1}{2\delta}\|f - v^{k+1}\|\right\} \quad (6)$$

The two steps are iterated until a desired solution, or stop criterion, is obtained. The algorithm interleaves a tomographic update that enforces the fidelity with the actual projection data and a denoising step that enforces the regularizer on the reconstruction image. For numerous regularizers there are very efficient algorithms for solving the denoising problem. Examples of regularizers that can be used in MBIR are total variation, Huber, q-GGMRF, generalized total variation, higher order regularizers, prior image compressed sensing (PICCS), and nonlocal variants of the aforementioned regularizers. Presently disclosed embodiments may be used in a tomographic update step by extending the correction images give by $Af^k - p$ before back projecting the correction images.

An ordered subsets procedure as described herein may be used with any reconstruction algorithm that involves sums over projection images (sonogram indices). Ordered subsets methods group projection image data into an ordered sequence of subsets that may be processed one at time to generate correction images which are then used to update the reconstruction image. As defined herein, one iteration is considered completed when the algorithm has cycled through all the projection images using all the subsets, which subsets may include one or more projection images. Alternatively, all the projection images may be treated as a set and processed altogether to generate an updated reconstruction image. The presently disclosed embodiments may be used in ordered set implementations where the correction images in the subset are extended and back projected to generate an updated reconstruction image.

For example, if desired, the algorithm disclosed herein may be applied to the set of captured projection images of an object using one x-ray source in a multi-source imaging system and their corresponding estimated 2D images. The algorithm may then be repeated using the set of captured projection images of the object using a second x-ray source in the multi-source imaging system, and so on for each additional source that may be used, as desired. Alternatively, a plurality of captured projection images may be divided into sets defined by other desired conditions such as set size, angular imaging range, or others, whereby the algorithm disclosed herein may be applied to each set. For example, in a 360° scan of an object 106 there may be captured and stored 600 projection images. Using a subset size of one (1)

a first one of the projection images is compared to a corresponding estimated 2D image to generate a first correction image. The correction image is extended by methods described herein and back projected into the current reconstruction image to generate an updated reconstruction image (which becomes the new current reconstruction image). The new current reconstruction image is used to generate a second estimated 2D image corresponding to a second one of the projection images to generate a second correction image, and the process repeats until all 600 actual projection images are processed which comprises one iteration of the method, which may then be repeated any finite number of times. Similarly, as another example embodiment, there may be 200 captured and stored images of the object 106, instead of 600, using a selected subset size of 10, instead of one (1). In this example, ten correction images are generated from each of ten projection images and their ten corresponding estimated 2D images. The ten correction images are each extended (extrapolated) and then back projected altogether into the current reconstruction image. In one embodiment, the ten extended correction images are summed together and back projected, to generate a new current reconstruction image, which is then used to generate a second set of ten estimated 2D images corresponding to the next ten projection images of the 200, and the process repeats until all 200 projection images are processed, in sets of ten, which comprises one iteration of the method, and which iteration may be repeated any finite number of times.

Figure 5:
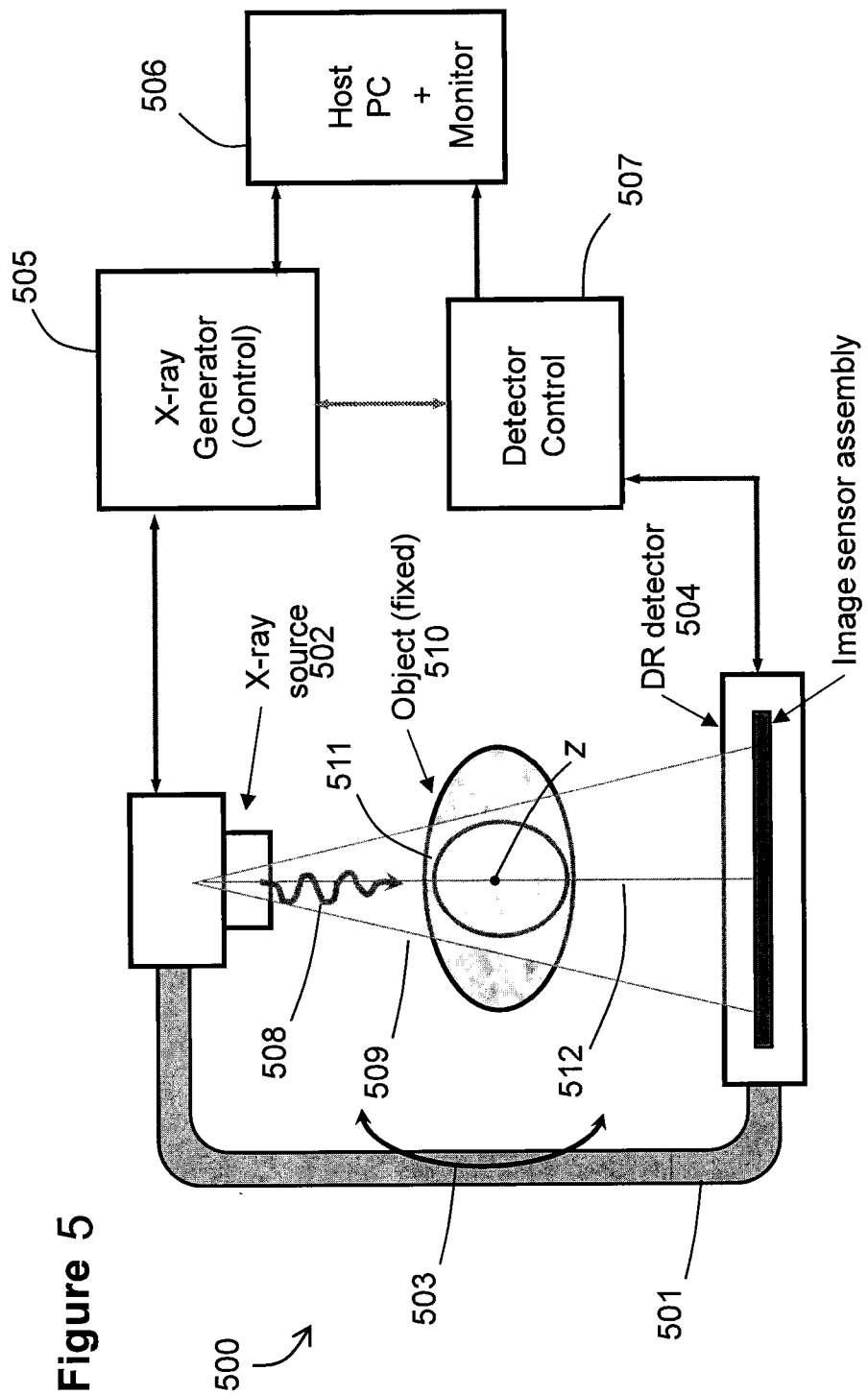
FIG. 5 is a schematic diagram of an exemplary CBCT imaging system.

FIG. 5 is a schematic diagram of an exemplary DR imaging system 500 that may be used to practice embodiments of the present invention disclosed herein. It will be understood that the exemplary DR imaging system 500 is not intended to deviate from the operational principles of the imaging system 100 as described herein. The DR imaging system 500 includes an x-ray source 502 configured to generate radiographic energy. The x-ray source 502 may include a single x-ray source or it may include the multi-source embodiment as illustrated in FIGS. 1A-B. The imaging system 500 further includes a generally planar DR detector 504, and a computer system 506 with digital monitor configured to display images captured by the DR detector 504. The DR detector 504 may include a two dimensional array of photosensor cells arranged in electronically addressable rows and columns. The DR detector 504 may be positioned to receive x-rays 508 passing through an object 510 during radiographic energy exposures, or radiographic firing of energy pulses, as emitted by the x-ray source 502 during an imaging scan. As shown in FIG. 5, the radiographic imaging system 500 may use an x-ray source 502 that emits collimated x-rays 508, e.g. a directed x-ray beam 509 such as a cone beam having a field of view, selectively aimed at and passing through a preselected region 511 of the object 510. The x-ray beam 509 may be attenuated by varying degrees along its plurality of rays according to the internal 3D structure of the object 510, whereby the attenuated rays are detected by the array of photosensitive cells in DR detector 504. The planar DR detector 504 is positioned, as much as possible, in a perpendicular relation to a substantially central path 512 of the plurality of rays 508 emitted by the x-ray source 502. The array of photosensitive cells (pixels) of DR detector 504 may be electronically read out (scanned) by their position according to column and row. As used herein, the terms "column" and "row" refer to the vertical and horizontal arrangement of the photosensor cells and, for clarity of description, it will be assumed that the rows extend horizontally and the columns extend vertically. However, the orientation of the columns and rows is arbitrary and does not limit the scope of any embodiments disclosed herein. Furthermore, the term "object" may be illustrated as a human patient in the description of FIG. 5, however, an object of a DR imaging system 100 or 500, as the term is used herein, may be a human, an animal, an inanimate object, or a portion thereof.

In one exemplary embodiment, the photosensitive cells of DR detector 504 may be read out one or more times during a scan to capture a plurality of projection images under control of a detector control circuit 507 so that the exposure data (digital images) from the array of detector 504 may be transmitted to the computer system 506. Each photosensitive cell in the DR detector 504 may independently detect and store an attenuation value which is generated by a charge level generated in proportion to an intensity, or energy level, of the attenuated radiographic radiation, or x-rays, received and absorbed in the photosensitive cells. Thus, each photosensitive cell, when read-out, provides information, or an attenuation value, defining a pixel of a radiographic image that may be digitally decoded by image processing electronics in the computer system 506 and displayed by the monitor for viewing by a user. Image processing electronics may be included within the DR detector 504 housing, whereby the radiographic images may be relayed to a computer system 506 by cable or wirelessly via electromagnetic wave transmission. As shown in FIG. 5, the source 502 and DR detector 504 may be affixed to a rotating mechanism such as a C-arm 501 which is configured to revolve the source 502 and detector 504 in either of the angular directions indicated by the arrow 503 about an imaging axis z that coincides with the object 510 while the DR detector captures a plurality of radiographic projection images of the object 510 at a number of angular imaging positions as the C-arm rotates about the object 510. Other rotational mechanisms may be employed to secure the source and detector in a diametrically opposed relation and to rotate about an imaged object, such as along a circular, curved, or C-shaped imaging path, by using a gantry, track, or turntable, for example.

The computer system 506 may communicate with a detector control circuit 507 and x-ray generator 504 over a connected cable (wired) or, as described herein, the DR detector 504 may be equipped with a wireless transmitter to transmit radiographic image data wirelessly to the computer system 506 for image processing therein. The detector control 507 may include a processor and electronic memory (not shown) to control operations of the DR detector 504 as described herein, or such control operations may be implemented using the computer system 506 by use of programmed instructions. Programmed instructions stored in memory accessible to computer system 506 may be executed to perform the reconstruction algorithms described herein. The computer system may also be used to control activation of the x-ray generator 505 and the x-ray source 502 during a radiographic exposure or scan, controlling an x-ray tube electric current magnitude, and thus the fluence of x-rays in x-ray beam 509, and/or the x-ray tube voltage, and thus the energy level of the x-rays in x-ray beam 509.

The DR detector 504 may transmit image (pixel) data to the monitor computer system 506 based on the radiographic exposure data received from its array of photosensitive cells. Alternatively, the DR detector may be equipped to process the image data and store it, or it may store raw unprocessed image data, in local or remotely accessible memory. The photosensitive cells in DR detector 504 may each include a sensing element sensitive to x-rays, i.e. it directly absorbs x-rays and generates an amount of charge carriers in proportion to a magnitude of the absorbed x-ray energy. A switching element may be configured to be selectively activated to read out the charge level of a corresponding x-ray sensing element. Alternatively, photosensitive cells of the indirect type may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, is disposed over the light sensitive sensing elements to convert incident x-ray radiographic energy to visible light energy. Thus, it should be noted that the DR detector 504, in the embodiments disclosed herein, may include an indirect or direct type of DR detector.

In one embodiment, the photosensitive cell array may be read out by sequentially switching rows of the photosensitive array to a conducting (on) state by means of read-out circuits. This digital image information may be subsequently processed by computer system 506 to yield a digital projection image which may then be digitally stored and immediately displayed on a monitor, or it may be displayed at a later time by accessing the digital electronic memory containing the stored image. A plurality of projection images captured and transmitted by the detector 504 may be accessed by computer system 506 to generate reconstructed 3D images using algorithms as described herein. The flat panel DR detector 504 having an imaging array as described herein is capable of both single-shot (e.g., static, projection) and continuous (e.g., fluoroscopic) image acquisition.

One embodiment of the computer system 506 further includes various software modules and hardware components to be implemented for substantially reducing truncated projection artifacts in computer tomography images using the methods described herein. According to one aspect of the current invention, truncated projection artifact reduction advantageously performs the reduction steps on cone beam data. In one embodiment, the artifact reduction method expands projection image data in a z-direction by adding a predetermined number of rows of additional data on top and bottom of captured image (measured) data. One embodiment of the artifact reduction method generates the additional data by copying data from the captured data in an edge row that corresponds to an edge of the detector. Another embodiment of the artifact reduction method generates the additional data by extrapolating data based upon the available captured data proximate the edge row that corresponds to an edge of the detector. Thus, one embodiment of the artifact reduction method generates the expanded data based upon the originally measured data and the additional data.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of determining a three dimensional spatial distribution of attenuation values of an object, the method comprising:
   obtaining an estimate of the spatial distribution of attenuation values;
   capturing a plurality of projection images of the object;
   generating one or more estimated projection images each associated with one of the plurality of captured projection images, the one or more estimated projection images based on the estimate of the spatial distribution of attenuation values;
   generating a correction image for each of the one or more estimated projection images and its associated captured projection image;
   extending each generated correction image along at least one of a column dimension or a row dimension of each generated correction image; and
   updating the estimate of the spatial distribution of attenuation values to generate a current estimate of the spatial distribution of attenuation values using the generated extended correction image or images.

2. The method of claim 1, further comprising:
   a) generating one or more current estimated projection images using a most recently updated estimate of the spatial distribution of attenuation values, the one or more current estimated projection images each associated with one of the plurality of captured projection images;
   b) generating a current correction image for each of the one or more current estimated projection images and its associated captured projection image;
   c) generating a current extended correction image for each generated current correction image;
   d) updating the current estimate of the spatial distribution of attenuation values using the generated current extended correction image or images; and
   e) repeating steps a)-d) until a stop criterion is satisfied.

3. The method of claim 1, wherein the step of capturing the plurality of projection images comprises using a movable radiation source fired at a plurality of different positions relative to the object.

4. The method of claim 1, wherein the step of capturing the plurality of projection images comprises using multiple radiation sources each fixed at a corresponding position relative to a detector, and individually firing the multiple radiation sources.

5. The method of claim 1, wherein the step of capturing the plurality of projection images comprises using an imaging system having a radiation source and a digital detector, and wherein the step of generating a plurality of estimated projection images includes calculating at least a portion of the estimated projection images based on a measured geometry of the imaging system.

6. The method of claim 2, further comprising determining if the current correction image satisfies the stop criterion.

7. The method of claim 2, further comprising determining whether the stop criterion is satisfied based on a step selected from the group consisting of measuring a difference between the current estimate of the spatial distribution of attenuation values and the most recently updated estimate of the spatial distribution of attenuation values, determining if a selected one or more of pixel values of the current correction image reaches a threshold, determining whether successive estimates of the spatial distribution of attenuation values are converging, and whether a preselected number of repetitions of the steps a)-d) are performed.

8. The method of claim 1, wherein the step of obtaining the estimate of the spatial distribution of attenuation values is selected from the group consisting of initializing the attenuation values to a preselected common value, initializing the attenuation values to a pre-stored plurality of attenuation values, and calculating the estimate of the spatial distribution of attenuation values based on a filtered back projection algorithm applied to one or more of the captured plurality of projection images of the object.

9. The method of claim 1, wherein the step of generating a correction image further comprises a step selected from the group consisting of determining a difference between the estimated projection images and their associated captured projection images, and determining a ratio between the estimated projection images and their associated captured projection images.

10. The method of claim 1, wherein the step of updating the estimate of the spatial distribution of attenuation values comprises backprojecting the extended correction image into the estimate of the spatial distribution of attenuation values.

11. The method of claim 1, wherein the step of generating an extended correction image is selected from the steps consisting of extending an edge of the at least one generated correction image linearly, extending an edge of the at least one generated correction image non-linearly, replicating and blurring an edge row or edge column of the at least one generated correction image data into a new row or column adjacent to the edge row or edge column, and extrapolating an edge row or edge column of the at least one generated correction image data into a new row or column adjacent to the edge row or edge column.

12. The method of claim 11, wherein the step of capturing the plurality of projection images of the object further comprises using a digital radiographic detector in a Cone Beam Computed Tomography (CBCT) imaging system and aligning two or more x-ray sources in a line that is parallel to a rotational axis of the CBCT imaging system.

13. A method of determining a spatial distribution of attenuation values of an object, the method comprising:
   obtaining an initial estimate of the spatial distribution of attenuation values of the object;
   capturing a plurality of projection images of the object using an imaging system having a preselected field of view, whereby each captured projection image comprises an associated field of view size;
   iteratively performing the steps of:
      generating one or more estimated projection images using the initial estimate of the spatial distribution of attenuation values once and thereafter using a current estimate of the spatial distribution of attenuation values;

comparing the one or more estimated projection images with corresponding ones of the captured projection images to generate one or more correction images corresponding to the field of view size;

extending the one or more generated correction images each along at least one of a column dimension or a row dimension of the one or more generated correction images beyond its corresponding field of view size; and generating the current estimate of the spatial distribution of attenuation values using the one or more extended correction images.

14. The method of claim 13, wherein the step of capturing the plurality of projection images comprises using a plurality of radiation sources each disposed at a different position relative to the object.

15. The method of claim 13, further comprising determining whether a stop criterion is reached, the stop criterion selected from the group consisting of whether a difference between a current estimate of the spatial distribution of attenuation values and a previous estimate of the spatial distribution of attenuation values has reached a preselected threshold value, whether one or more pixels of the one or more of the correction images reaches a threshold, whether successive estimates of the spatial distribution of attenuation values are converging, and whether a preselected number of the iteratively performed steps are completed.

16. The method of claim 13, wherein the step of obtaining the initial estimate of the spatial distribution of attenuation values is selected from the group consisting of initializing the attenuation values to a preselected common value, initializing the attenuation values to a pre-stored plurality of attenuation values, and calculating the estimate of the spatial distribution of attenuation values based on a filtered back projection algorithm applied to one or more of the captured plurality of projection images of the object.

17. A method of determining a three dimensional spatial distribution of attenuation values of an object using a radiographic imaging system, the method comprising:

obtaining an estimate of the spatial distribution of attenuation values;

capturing a plurality of projection images of the object using two or more x-ray sources each positioned at a different location in the imaging system;

generating a plurality of estimated projection images each corresponding to one of the captured plurality of projection images using two or more x-ray sources, the plurality of estimated projection images based on the estimate of the spatial distribution of attenuation values;

generating a correction image for each of the plurality of estimated projection images and their corresponding captured projection images;

extending each of the plurality of generated correction images along at least one of a column dimension or a row dimension of each of the plurality of generated correction images; and updating the estimate of the spatial distribution of attenuation values using the extended correction images.

18. The method of claim 17, wherein the step of generating an extended correction image is selected from the steps consisting of extending an edge row or edge column of the correction image linearly, extending an edge row or edge column of the correction image non-linearly, replicating and blurring an edge row or edge column of the correction image into a new row or new column adjacent to the edge row or edge column, and extrapolating the edge row or the edge column of the correction image data into the new row or new column adjacent to the edge row or edge column.

19. The method of claim 18, wherein the steps of generating a plurality of estimated projection images, generating a correction image, generating an extended correction image, and updating the estimate of the spatial distribution of attenuation values are repeated until a stop criterion is reached, the stop criterion selected from the group consisting of whether a difference between a current estimate of the spatial distribution of attenuation values and a previous estimate of the spatial distribution of attenuation values has reached a preselected threshold value, whether one or more pixels of the one or more of the correction images reaches a threshold, whether successive estimates of the spatial distribution of attenuation values are converging, and whether a preselected number of repetitions of the repeated steps are completed.

* * * * *